United States Patent [19]

Kampe et al.

[11] 4,076,829

[45] Feb. 28, 1978

[54] AMINOPROPANOL COMPOUNDS AND COMPOSITIONS FOR THE TREATMENT OF CARDIAC AND CIRCULATORY DISEASES

[75] Inventors: Wolfgang Kampe, Heddesheim; Kurt Stach, Mannheim-Waldhof; Max Thiel, Mannheim; Wolfgang Bartsch, Viernheim; Karl Dietmann, Mannheim-Vogelstang; Egon Roesch, Mannheim; Wolfgang Schaumann, Heidelberg, all of Germany

[73] Assignee: Boehringer Mannheim GmbH, Mannheim, Germany

[21] Appl. No.: 626,512

[22] Filed: Oct. 28, 1975

[30] Foreign Application Priority Data

| | | |
|---|---|---|
| Nov. 16, 1974 | Germany | 2454406 |
| Jun. 27, 1975 | Germany | 2528771 |
| Feb. 11, 1975 | Germany | 2505681 |
| Feb. 26, 1975 | Germany | 2508251 |

[51] Int. Cl.[2] A61K 31/40; C07D 209/14

[52] U.S. Cl. 424/274; 260/326.12 R; 260/326.13 R; 260/326.14 R; 260/326.15; 260/326.16

[58] Field of Search 260/326.15; 424/274

[56] References Cited

U.S. PATENT DOCUMENTS

| | | | |
|---|---|---|---|
| 3,471,515 | 10/1969 | Troxler et al. | 260/326.15 |
| 3,479,371 | 11/1969 | Troxler et al. | 260/326.15 |
| 3,696,120 | 10/1972 | Troxler | 260/326.15 |
| 3,696,121 | 10/1972 | Troxler | 260/326.15 |
| 3,705,907 | 12/1972 | Troxler | 260/326.15 |
| 3,751,429 | 8/1973 | Seemann et al. | 260/326.15 |
| 3,758,502 | 9/1973 | Seemann et al. | 260/326.15 |
| 3,808,231 | 4/1974 | Seemann et al. | 260/326.15 |

OTHER PUBLICATIONS

Crowther et al., "Chem. Abstracts," vol. 76, No. 148741g (1972).

Crowther et al., "J. Med. Chem.," vol. 11, pp. 1009-1013 (1968).

*Primary Examiner*—Ethel G. Love

*Attorney, Agent, or Firm*—Burgess, Dinklage & Sprung

[57] ABSTRACT

New aminopropanol compounds of the formula (I)

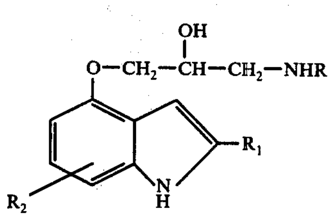

wherein

R is lower alkyl, cycloalkyl or alkylthioalkyl, $R_1$ is hydrogen or lower alkyl, hydroxyalkyl, pivaloyloxyalkyl, alkoxyalkyl, alkoxycarbonyl, carboxyl or $-CONR_3R_4$, in which $R_3$ and $R_4$ which can be the same or different, represent hydrogen or lower alkyl, and $R_2$ is lower alkyl, hydroxyalkyl, alkoxyalkyl or pivaloyloxyalkyl or, when R is alkylthioalkyl or $R_1$ is pivaloyloxyalkyl, $R_2$ can also be hydrogen and the pharmacologically acceptable salts thereof; are outstandingly effective in the treatment or prophylaxis of cardiac and circulatory diseases.

19 Claims, No Drawings

AMINOPROPANOL COMPOUNDS AND COMPOSITIONS FOR THE TREATMENT OF CARDIAC AND CIRCULATORY DISEASES

The present invention is concerned with new aminopropanol compounds, with therapeutic compositions containing them, and with methods for the treatment of cardiac and circulatory diseases using such compounds.

The new aminopropanol derivatives according to the present invention are compounds of the formula (I)

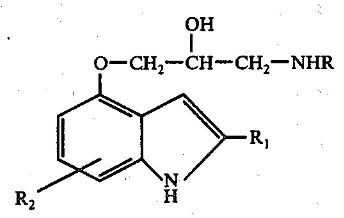

wherein

R is lower alkyl, cycloalkyl or alkylthioalkyl, $R_1$ is hydrogen or lower alkyl, hydroxyalkyl, pivaloyloxyalkyl, alkoxyalkyl, alkoxycarbonyl, carboxyl or $-CONR_3R_4$, in which $R_3$ and $R_4$ can be the same or different, represent hydrogen or lower alkyl, and $R_2$ is lower alkyl, hydroxyalkyl, alkoxyalkyl or pivaloyloxyalkyl or, when R is alkylthioalkyl or $R_1$ is pivaloyloxyalkyl, $R_2$ can also be hydrogen and the pharmacologically acceptable salts thereof.

The alkyl radicals in the definitions of the substituents R, $R_1$, $R_2$, $R_3$, and $R_4$ can contain up to 6 and preferably up to 5 carbon atoms and can be straight or branched chained, the alkyl radicals in the definitions of the substituents R preferably being branched chained. The cycloalkyl radical R can contain 3 to 6 and preferably 3 or 4 carbon atoms.

The new compounds according to the present invention, as well as the pharmacologically compatible salts thereof, bring about an inhibition of the adrenogenic β-receptors and can, therefore, be used for the treatment or prophylaxis of cardiac and circulatory diseases.

The new compounds (I) according to the present invention can be prepared, for example, by one of the following methods:

a. reaction of a compound of the general formula:

(II),

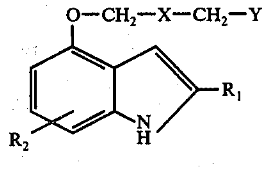

with a compound of the general formula:

$$Z - R' \quad \text{(III)},$$

in which $R_1$ and $R_2$ have the same meaning as above,

R' is a mercaptoalkyl radical or has the same meaning as R, one of the symbols

Y and Z stands for an amino group and the other for a reactive residue and

X is the group $=C=O$ or $=CH-A$ whereby

A is a hydroxyl group or, together with Y, can also signify an oxygen atom; or b. reaction of a compound of the general formula:

(IV),

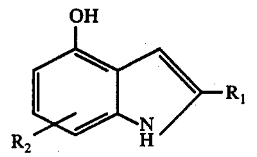

wherein $R_1$ and $R_2$ have the same meanings as above, with a compound of the general formula:

$$Y'-CH_2-X-CH_2-NHR' \quad \text{(V)},$$

wherein R' and X have the same meanings as above and Y' is a reactive residue; or c. for the case in which R is an alkylthioalkyl radical, reaction of a compound of the general formula:

(VI),

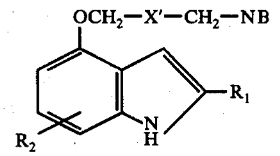

wherein $R_1$ and $R_2$ have the same meanings as above, B is a lower alkylene radical and X' signifies the group $=C=O$ or $=CHOH$, with a compound of the general formula:

$$HS-R_5 \quad \text{(VII)},$$

wherein $R_5$ is a hydrogen atom or a lower alkyl radical; or d. for the case in which $R_1$ and/or $R_2$ represents a pivaloyloxyalkyl radical, reaction of a compound of the general formula:

(VIII),

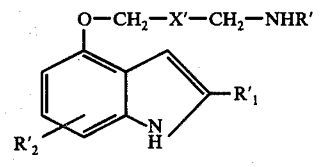

wherein R' and X' have the same meanings as above and $R'_1$ and/or $R'_2$ represent a hydroxyalkyl group, whereby one of these symbols $R'_1$ or $R'_2$ can also have the same meaning as $R_1$ or $R_2$, with pivalic acid or with a reactive derivative thereof, whereafter, when R' is a mercaptoalkyl radical or $R_5$ is a hydrogen atom, alkylation is subsequently carried out on the sulfur atom and when X or X' is a $=C=O$ group, reduction is subsequently carried out and, if desired, in the compound thus obtained of the general formula (I), one of the particular substituents $R_1$ is converted into a different substituent $R_1$ by saponification, esterification, transesterification, acylation or alkylation.

The compounds of general formula (I) obtained according to processes (a), (b), (c) or (d) can, if desired, be subsequently converted into their pharmacologically compatible salts.

The alkyl radicals in the definitions of the substituents $R_5$ and B can be contain up to 6 and preferably up to 5 carbon atoms and can straight or branched chained, preferably being branched chained. The cycloalkyl radical $R_5$ can contain 3 to 6 and preferably 3 or 4 carbon atoms.

The active residues Y, Z and Y' in compounds of general formulae (II), (III), and (V) are, in particular, acid residues, for example residues of hydrohalic or sulfonic acids.

Compounds of general formula (II) are described, for example, in Helv. Chim. Acta, 54 2418/1971 and amines of general formula (III) are described in German Pat. No. 2,045,905. Compounds of general formula (VI) can be obtained, for example, by the reaction of compounds of general formula (II) with compounds of the general formula

HNB, wherein B has the same meaning as above.

The processes according to the present invention are preferably carried out in an organic solvent which is inert under the reaction conditions, for example, toluene, dioxan, ethylene glycol dimethyl ether, ethanol, n-butanol or dimethylformamide, optionally in the presence of an acid-binding agent. However, the reaction can also be accomplished, after mixing the reaction components, by leaving the reaction mixture to stand at ambient temperature or by heating.

The reaction of compounds of general formula (IV) with compounds of general formula (V) according to process (b) is preferably carried out with the exclusion of oxygen, in the presence of an acid acceptor. However, an alkali metal salt of the hydroxy compound of general formula (IV) can also be used.

The introduction of the pivaloyl radical into the hydroxyalkyl radical of compounds of general formula (VIII) according to process (d) takes place under the usual conditions of acylation, for example, by the reaction of compounds of general formula (VIII) with pivaloyl chloride, with cooling, in the presence of a base, such as pyridine.

The S-alkylation for the case is which R' in general formulae (III), (V) and (VIII) signifies a mercaptoalkyl radical or $R_5$ in general formula (VII) signifies a hydrogen atom, is also preferably carried out in a solvent of the above-mentioned type, with the exclusion of oxygen, using a conventional S-alkylation agent.

The reduction of the group =C—O possibly to be carried out can be achieved by means of sodium borohydride or by catalytic hydrogenation in the presence of a noble metal catalyst.

The subsequent conversion of a radical $R_1$ into a different radical $R_1$ which it may be desired to carry out, can take place in conventional manner by saponification, esterification, transesterification, acylation or alkylation. For example, a compound of general formula (I), in which $R_1$ is an alkoxycarbonyl radical, can be subsequently saponified to give the corresponding carboxylic acid of general formula (I), in which $R_1$ is a carboxyl radical; this can be carried out in the usual way, preferably in dilute aqueous alkali metal hydroxide solution.

For the conversion of compounds of general formula (I) into their pharmacologically compatible salts, these are reacted, preferably in an organic solvent, with an equivalent amount of an inorganic or organic acid, for example, hydrochloric acid, hydrobromic acid, phosphoric acid, sulfuric acid, acetic acid, citric acid, maleic acid or benzoic acid.

For the preparation of pharmaceutical compositions, the compounds of general formula (I) are mixed in known manner with appropriate pharmaceutical carrier substances, and with aroma, flavoring and coloring materials and formed, for example, into tablets or dragees or, with the addition of appropriate adjuvants, are suspended or dissolved in water or an oil, for example in olive oil.

The new compounds of general formula (I) according to the present invention and the salts thereof can be administered enterally or parenterally in liquid or solid form. As injection medium, water is preferably used which contains the additives usual for injection solutions, such as stabilizing agents, solubilizing agents or buffers. Additives of this type include, for example, tartrate and citrate buffers, ethanol, complex-forming agents (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegatible fats and solid high molecular weight polymers (such as polyethylene glycols); compositions suitable for oral administration can, if desired, contain flavoring and sweetening materials.

Apart from the compounds mentioned in the following specific Examples, preferred compounds according to the present invention include the following:

4-[2-hydroxy-3-(1-propylthio-2-methylisopropylamino)-propoxy]-indole;
4-[2-hydroxy-3-(1-methylthiolisopropylamino)-propoxy]- indole;
4-[2-hydroxy-3-(2-methylthio-2-methylpropylamino)-propoxy]-indole;
4-[2-hydroxy-3-(1-methylthioisopropylamino)-propoxy]-2-methyl-indole;
4-[2-hydroxy-3-(1-methylthioisopropylamino)-propoxy]-2-hydroxymethyl-indole;
4-[2-hydroxy-3-(1-methylthioisopropylamino)-propoxy]-2-ethoxycarbonyl-indole;
4-[2-hydroxy-3-(1-methylthioisopropylamino)-propoxy]-2-carbamoyl-indole;
4-[2-hydroxy-3-(1-methylthioisopropylamino)-propoxy]-2-dimethylaminocarbonyl-indole;
4-[2-hydroxy-3-(1-methylthioisopropylamino)-propoxy]-2-carboxy-indole;
4-[2-hydroxy-3-(1-methylthioisopropylamino)-propoxy]-2-methoxymethyl-indole;
4-(2-hydroxy-3-sec.-butylaminopropoxy)-pivaloyloxymethyl-indole;
4-(2-hydroxy-3-cyclobutylaminopropoxy)-2-pivaloyloxymethyl-indole;
4-(2-hydroxy-3-tert.-pentylaminopropoxy)-2-pivaloyloxymethyl-indole;
4-(2-hydroxy-3-sec.-butylaminopropoxy)-6-hydroxymethyl-indole;
4-[2-hydroxy-3-(1-methylthioisopropylamino)-propoxy]-6-hydroxymethyl-indole;
4-[2-hydroxy-3-(1-methylthio-2-methylisopropylamino)-propoxy]-6-hydroxymethyl-indole;

4-[2-hydroxy-3-(1-ethylthio-2-methyl-isopropylamino)-propoxy]-6-hydroxymethyl-indole;
4-[2-hydroxy-3-(1-isopropylthio-2-methyl-isopropylamino)-propoxy]-6-hydroxymethyl-indole;
4-(2-hydroxy-3-sec.-butylaminopropoxy)-6-methyl-indole;
4-[2-hydroxy-3-(1-methylthioisopropylamino)-propoxy]-6-methyl-indole;
4-[2-hydroxy-3-(1-ethylthio-2-methyl-isopropylamino)-propoxy]-6-methyl-indole;
4-[2-hydroxy-3-(1-isopropylthio-2-methyl-isopropylamino)-propoxy]-6-methyl-indole;
4-(2-hydroxy-3-isopropylaminopropoxy)-6-pivaloyloxymethyl-indole;
4-(2-hydroxy-3-sec.-butylaminopropoxy)-6-pivaloyloxymethyl-indole;
4-[2-hydroxy-3-(1-methylthioisopropylamino)-propoxy]-6-pivaloyloxymethyl-indole;
4-[2-hydroxy-3-(1-methylthio-2-methyl-isopropylamino)-propoxy]-6-pivaloyloxymethyl-indole;
4-[2-hydroxy-3-(1-ethylthio-2-methylisopropylamino)-propoxy]-6-pivaloyloxymethyl-indole;
4-(2-hydroxy-3-isopropylaminopropoxy)-6-methoxymethyl-indole.

The following examples are given for the purpose of illustrating the present invention.

EXAMPLE 1

Preparation of
4-[2-hydroxy-3-(1-methylthio-2-methylisopropylamino)-propoxy]-indole cl Variant I A mixture of 5.7 g. 4-(2,3-epoxypropoxy)-indole and 7.1 g. 1-methylthio-2-methylpropyl-2-amine was stirred for 48 hours at ambient temperature. The viscous reaction mixture was dissolved in about 50 ml. diethyl ether and subsequently mixed with ligroin. After filtering with suction and drying the crystals thereby obtained, there were obtained 8.5 g (92% of theory) chromatographically pure 4- [2-hydroxy-3-(1-methylthio-2-methylisopropylamino)-propoxy]-indole; m.p. 119° 14 120° C.

Variant II

A mixture of 1.9 g. 4-(2,3-epoxypropoxy)-indole and 5 ml. 2,2-dimethyl-aziridine was stirred overnight at ambient temperature and subsequently for a further 4 hours at 40° - 50° C. Excess 2,2-dimethyl-aziridine was removed in a vacuum. The residue was taken up in 15 ml. isopropanol. This solution was added slowly, with cooling to 0° - 5° C., to a solution, saturated at 0° C., of methyl mercaptan in about 15 ml. isopropanol. After standing for about 20 hours at ambient temperature, excess methyl mercaptan was removed by blowing nitrogen through the reaction mixture. The isopropanol solution was mixed with 1.3 g. benzoic acid and subsequently diluted with 100 ml. diethyl ether. After filtering off with suction and drying the precipitate obtained, there were obtained 2.9 g. of a product with a melting point of 155° - 157° C. By the partial evaporation of the mother liquors, there was obtained a second crystallizate (0.8 g.; m.p. 155° - 156° C). The total yield was 3.7 g. (86% of theory) 4-[2-hydroxy-3-(1-methylthio-2-methylisopropylamino)-propoxy]-indole.

Preparation of the benzoate 3.1 g. (0.01 mole) 4-[2-hydroxy-3-(1-methylthio-2-methylisopropylamino)-propoxy]-indole were dissolved in 50 ml. ethyl acetate and mixed with an equivalent amount of benzoic acid, dissolved in a little ethyl acetate. The precipitate which slowly separates out was, after some time, filtered off with suction and dried. There were obtained 4.0 g. (93% of theory) 4-[2-hydroxy-3-(1-methylthio-2-methylisopropylamino)-propoxy]-indole benzoate; m.p. 155° C.

EXAMPLE 2

Preparation of
4-[2-hydroxy-3-(1-ethylthio-2-methylisopropylamino)-propoxy]-indole A mixture of 1.9 g. 4-(2,3-epoxypropoxy)-indole and 3.5 ml. 2,2-dimethyl-aziridine was left to stand for 3 days at ambient temperature. Excess 2,2-dimethyl-aziridine was removed in a vacuum. The residue was taken up in 10 ml. ethyl mercaptan and the solution left to stand for 2 days at ambient temperature. Subsequently, the reaction mixture was evaporated in a vacuum and the residue dissolved in diethyl ether and a a little ethyl acetate. After the addition of 1.2 g. benzoic acid, dissolved in 20 ml diethyl ether, a precipitate was formed. This was filtered off with suction and recrystallized from isopropanol. There were obtained 2.4 g. (54% of theory) 4-[2-hydroxy-3-(1-ethylthio-2-methylisopropylamino)-propoxy]-indole in the form of its benzoate; m.p. 161° C.

EXAMPLE 3

Preparation of
4-[2-hydroxy-3-(1-isopropylthio-2-methylisopropylamino)-propoxy]-indole A mixture of 1.7 g. 4-(2,3-epoxypropoxy)-indole and 3.5 ml. 2,2-dimethyl-aziridine was left to stand for 3 days at ambient temperature. Excess 2,2-dimethyl-aziridine was removed in a vacuum. The residue was taken up in 20 ml. isopropyl mercaptan and the solution heated to the boil for 20 hours. Subsequently, the reaction mixture was evaporated in a vacuum and worked up in a manner analogous to that described in Example 2. There was obtained 1.5 g. (34% of theory) 4-[2-hydroxy-3-(1-isopropylthio-2-methyl-isopropylamino)-propoxy]-indole in the form of its benzoate; m.p. 132° - 133° C.

EXAMPLE 4

Preparation of
4-[2-hydroxy-3-(1-methylthio-2-methylisopropylamino)-propoxy]-2-methyl-indole A mixture of 5.1 g. 4-(2,3-epoxypropoxy)-2-methylindole and 5 ml. 2,2-dimethyl-aziridine was left to stand at ambient temperature for 3 days. Excess 2,2-dimethylaziridine was distilled off in a vacuum. The residue was dissolved in 20 ml. isopropanol which had been saturated at 0° - 5° C. with methyl mercaptan. The reaction mixture was left to stand for 2 days at ambient temperature and subsequently evaporated. The residue was dissolved in 30 ml. ethyl acetate and the solution mixed with 3.0 g. benzoic acid in 10 ml. diethyl ether. The precipitate obtained was filtered off with suction and recrystalized from about 30 ml. isopropanol. After filtering off with suction and drying, there were obtained 2.0 g. (18% of theory) 4-[2-hydroxy-3-(1-methylthio-2-methylisopropylamino)-propoxy]-2-methyl-indole in the form of its benzoate; m.p. 151° - 152° C.

EXAMPLE 5

Preparation of 4-[2-hydroxy-3-(1-methylthio-2-methylisopropylamino)-propoxy]-2-hydroxymethyl-indole A mixture of 8.2 g. 4-(2,3-epoxypropoxy)-2-hydroxymethyl-indole and 5.35 g. 1-methylthio-2-methylpropyl-2-amine was left to stand for 24 hours at ambient temperature and subsequently taken up in a mixture of diethyl ether and ethyl acetate. The organic phase was shaken out with dilute acetic acid and discarded. The aqueous acetic acid phase was rendered alkaline and extracted with diethyl ether/ethyl acetate. The solution was washed with water, dried and evaporated. The residue was dissolved in 25 ml. ethyl acetate and the solution mixed with 4.1 g. benzoic acid in 25 ml. ethyl acetate. The first crystals consist almost exclusively of the benzoate of 1-methylthio-2-methylpropyl-2-amine and were discarded. After partial evaporation of the mother liquor and the addition of some diethyl ether, there were obtained 5.2 g. of crude product. This was recrystallized from 100 ml. ethyl acetate. After filtering with suction and drying, there were obtained 3.5 g. (22% of theory) 4-[2-hydroxy-3-(1-methylthio-2-methylisopropylamino)-propoxy]-2-hydroxymethyl-indole in the form of its benzoate; m.p. 124° - 126° C.

EXAMPLE 6

Preparation of 4-[2-hydroxy-3-(1-methylthio-2-methylisopropylamino)-propoxy]-2-pivaloyloxymethyl-indole 5.3 g. 4-(2,3-epoxypropoxy)-2-pivaloyloxymethyl-indole and 2.5 g. 1-methylthio-2-methylpropyl-2-amine were heated in 5 ml. isopropanol for 36 hours at 50° C. Thereafter, the reaction mixture was evaporated in a vacuum and the residue partitioned between diethyl ether and dilute acetic acid. The acetic acid phase was rendered alkaline and extracted with diethyl ether. The ethereal solution was dried, evaporated somewhat and mixed with benzoic acid. The solution was evaporated in a vacuum and the residue was recrystallized from a little isopropanol. After filtering off with suction and drying, there was obtained 1.5 g. (about 16% of theory) 4-[2-hydroxy-3-(1-methylthio-2-methyl-isopropylamino)propoxy]-2-pivaloyloxymethyl-indole in the form of its benzoate; m.p. 119° - 121° C.

EXAMPLE 7

Preparation of 4-[2-hydroxy-3-(1-methylthio-2-methylisopropylamino)-propoxy]-2-ethoxycarbonyl-indole 5.2 g. 4-(2,3-epoxypropoxy)-2-ethoxycarbonyl-indole and 2.6 g. 1-methylthio-2-methylpropyl-2-amine were stirred, with gentle warming, until a homogeneous mixture was formed. After standing overnight at ambient temperature, the reaction mixture was partitioned between diethyl ether/ethyl acetate and dilute acetic acid. The acidic phase was rendered alkaline with potassium carbonate and extracted with ethyl acetate/diethyl ether. The extract was dried, evaporated and the residue subsequently mixed twice with toluene and evaporated each time. The residue was dissolved in about 50 ml. ethyl acetate/diethyl ether and mixed with 1.7 g. benzoic acid. The precipitate obtained was filtered off with suction and dried. There were obtained 4.1 g. (about 40% of theory) 4-[2-hydroxy-3-(1-methylthio-2-methylisopropylamine)-propoxy]-2-ethoxycarbonyl-indole in the form of its benzoate, which sinters at about 85° C.

EXAMPLE 8

Preparation of 4-[2-hydroxy-3-(1-methylthio-2-methylisopropylamino)-propoxy]-2-carbamoyl-indole 9.5 g. 4-(2,3-epoxypropoxy)-2-carbamoyl-indole and 4.4 g. 1-methylthio-2-methylpropyl-2-amine were stirred together, with gentle warming, until a homogeneous mixture was formed. The reaction mixture was left to stand overnight at ambient temperature and then triturated with diethyl ether. The solid residue was filtered off with suction and taken up in 100 ml. isopropanol. To this was added a solution of 3.5 g. maleic acid in 50 ml. isopropanol. The precipitate which slowly separates out was filtered off with suction and dried. There were obtained 3.8 g. (about 23% of theory) 4-[2-hydroxy-3-(1-methylthio-2-methylisopropylamino)-propoxy]-2-carbamoyl-indole in the form of its maleate; m.p. 119° - 121° C.

EXAMPLE 9

Preparation of 4-[2-hydroxy-3-(1-methylthio-2-methylisopropylamino)-propoxy]-2-dimethylaminocarbonyl-indole 9.2 g. 4-(2,3-epoxypropoxy)-2-dimethylaminocarbonyl-indole and 5 ml. 1-methylthio-2-methylpropyl-2-amine were stirred together, with gentle warming, until a homogeneous mixture was formed. After standing for 2 days at ambient temperature, the reaction mixture was triturated three times with diethyl ether. The etheral extract was discarded and the residue was dissolved in ethyl acetate and treated with active charcoal. After the addition of 2.1 g. benzoic acid, dissolved in some ethyl acetate, a precipitate was obtained. This was filtered off with suction and recrystallized twice from some methanol. There were obtained 2.7 g. (18% of theory) 4-[2-hydroxy-3-(1-methylthio-2-methylisopropylamino)-propoxy]-2-dimethylaminocarbonyl-indole in the form of its benzoate; m.p. 114° 14 116° C.

EXAMPLE 10

4-[2-hydroxy-3-(1-methylthio-2-methylisopropylamino)-propoxy]-2-carboxy-indole 2.7 g. 4-[2-hydroxy-3-(1-methylthio-2-methylisopropylamino)-propoxy]-2-ethoxycarbonyl-indole (see Example 7) and 0.4 g. potassium hydroxide were dissolved in a mixture of 25 ml. ethanol and 5 ml. water. The solution was maintained at ambient temperature for 24 hours and then at 50° C. for 3 hours. Subsequently, the pH was adjusted to about 3.5 with 2N hydrochloric acid. The oil which thereby separates out crystallized upon triturating with ethyl acetate and n-butanol. After filtering off the crystals with suction and drying them, there was obtained 1.6 g. (65% of theory) 4-[2-hydroxy-3-(1-methylthio-2-methylisopropylamino)-propoxy]-2-carboxy-indole hydrate; m.p. 163° C.

EXAMPLE 11

Preparation of 4-[2-hydroxy-3-(1-methylthio-2-methylisopropylamino)-propoxy]-2-methoxymethyl-indole 1.4 g. 4-(2,3-epoxypropoxy)-2-methoxymethyl-indole and 0.72 g. 1-methylthio-2-methylpropyl-2-amine were stirred, with gentle warming, to give a homogeneous mixture. After standing for 2 days at ambient temperature, the reaction mixture was dissolved in diethyl ether and the ethereal phase was extracted with 1N tartaric acid. The organic phase was discarded and the aqueous phase was rendered weakly alkaline with an aqueous solution of sodium bicarbonate and extracted with ether. After drying and evaporating the ethereal solution, the residue was dissolved in a little diethyl ether/ethyl acetate (1:1 v/v) and the solution mixed with 0.6 g. benzoic acid in 5 ml. diethyl ether. The supernatant was decanted off from the initially oily precipitate obtained. The oil crystallizes upon triturating with ethyl acetate (0.5 g.). A further 0.8 g. of crude product was obtained from the decantate after seeding. After recrystallization of the combined crude product from 10 ml. isopropanol, there was obtained 1.0 g. (35% of theory) 4-[2-hydroxy-3-(1-methylthio-2-isopropylamino)-propoxy]-2-methoxymethyl-indole in the form of its benzoate; m.p. 104°-107° C.

EXAMPLE 12

Preparation of 4-(2-hydroxy-3-tert.-butylaminopropoxy)-2-pivaloyloxymethyl-indole 3.1 g. 4-(2,3-epoxypropoxy)-2-pivaloyloxymethyl-indole were dissolved in 25 ml. tert.-butylamine. The mixture was left to stand for 2 days at ambient temperature and then evaporated in a vacuum. The residue was partitioned between dilute acetic acid and diethyl ether. The ethereal phase was discarded, the acetic acid solution was rendered weakly alkaline and then extracted several times with diethyl ether. The ethereal solution was dried and evaporated. The crystalline residue (1.9 g.) was again taken up in diethyl ether and the solution mixed with 0.63 g. benzoic acid. The precipitate which slowly separated out was, after some time, filtered off with suction and dried. There was obtained 2.0 g. (40% of theory) chromatographically pure 4-(2-hydroxy-3-tert. butylaminopropoxy)-2-pivaloyloxymethyl-indole in the form of its benzoate; m.p. 149° - 150° C.

The 4-(2,3-epoxypropoxy)-2-pivaloyloxymethyl-indole used as starting material can be prepared as follows:

11.5 g. 4-(2,3-epoxypropoxy)-2-hydroxymethyl-indole (see U.S. Pat. No. 3,705,907) were dissolved in 100 ml. pyridine. To this solution were added dropwise, while cooling to 0° - 5° C., 6.5 g. (6.7 ml.) pivaloyl chloride. After an hour, the reaction mixture was poured on to ice and extracted with diethyl ether. The ethereal solution was successively washed with dilute sulfuric acid, aqueous sodium bicarbonate solution and water. After drying and treating with active charcoal, the solution was filtered and evaporated. The residue (13 g.; 82% of theory) crystallized upon triturating with diethyl ether/ligroin to give 4-(2,3-epoxypropoxy)-2-pivaloyloxymethyl-indole; m.p. 129° - 131° C.

EXAMPLE 13

Preparation of 4-(2-hydroxy-3-isopropylaminopropoxy)-2-pivaloyloxymethyl-indole According to the process described in Example 12, from 2.6 g. 4-(2,3-epoxypropoxy)-2-pivaloyloxymethyl-indole and 10 ml. isopropylamine, there was obtained 1.1 g. (27% of theory) 4-(2-hydroxy-3-isopropylaminopropoxy)-2-pivaloyloxymethyl-indole in the form of its benzoate; m.p. 133° - 135° C.

EXAMPLE 14

Preparation of 4-(2-hydroxy-3-cyclopropylaminopropoxy)-2-pivaloyloxymethyl-indole According to the process described in Example 12, from 2.0 g. 4-(2,3-epoxypropoxy)-2-pivaloyloxymethyl-indole and 4 ml. cyclopropylamine, there were obtained 2.7 g. (85% of theory) 4-(2-hydroxy-3-cyclopropylaminopropoxy)-2-pivaloyloxymethyl-indole in the form of its benzoate; m.p. 146° - 147° C.

EXAMPLE 15

Preparation of 4-(2-hydroxy-3-tert.-butylaminopropoxy)-6-hydroxymethyl-indole 5 g. 4-(2,3-epoxypropoxy)-6-hydroxymethyl-indole were dissolved in 25 ml. tert.-butylamine. The mixture was left to stand for 2 days at ambient temperature, subsequently boiled gently for about an hour and then evaporated in a vacuum. The residue was partitioned between dilute acetic acid and diethyl ether. The ethereal phase was discarded and the acetic acid solution was rendered alkaline and then shaken out with ether. After drying and evaporating the ethereal phase, the base thereby obtained was recrystallized from a little ethyl acetate/diethyl ether (3.3 g. of base; m.p. 129° - 131° C). 3.0 g. of this base were dissolved in a mixture of about 100 ml. ethyl acetate and 20 ml. isopropanol. Upon the addition of 1.2 g. benzoic acid, the benzoate slowly precipitates out. After filtering off with suction and drying, there were obtained 3.4 g. (41% of theory) 4-(2-hydroxy-3-tert.-butylaminopropoxy)-6-hydroxymethyl-indole in the form of its benzoate; m.p. 190° - 191° C.

The 4-(2,3-epoxypropoxy)-6-hydroxymethyl-indole used as starting material is prepared as follows:

4-Acetoxy-6-methoxycarbonyl-indole, obtained by the modification of a process described by N.R. El-Rayyes (J. prakt. Chem., 315, 295/1973), was saponified with sodium methylate, with the exclusion of oxygen, to give 4-hydroxy-6-methoxycarbonyl-indole. 22.2 g. of the 4-hydroxy-6-methoxycarbonyl-indole thus obtained, 16.5 g. dry potassium carbonate and 15.9 ml. benzyl chloride were heated for 3 hours to 80°-90° C., while stirring, in 200 ml. anhydrous dimethyl formamide. About 100-150 ml. dimethyl formamide were evaporated off in a vacuum and the residue is mixed with water and diethyl ether. The ethereal phase was separated off and the aqueous phase extracted several times with diethyl ether. The combined ethereal extracts were dried, clarified with active charcoal and evaporated. The crystallized residue was, with the addition of active charcoal, recrystallized from ethanol. There were obtained 18.0 g. (53.5% of theory) of almost colorless crystals; m.p. 160° - 162° C.

A solution of 24.5 g. of the 4-benzyloxy-6-methoxycarbonylindole thus obtained in 150 ml. anhydrous tetrahydrofuran was added dropwise, while stirring and cooling to 15° - 20° C., into a suspension of 5.3 g. lithium aluminium hydride in 150 ml. anhydrous tetrahydrofuran. After 4 hours, excess reducing agent was decomposed by the addtion of 25 ml. of a saturated aqueous solution of solution chloride. The precipitate obtained was filtered off with suction and washed with diethyl ether. The filtrate was dried, treated with active charcoal and evaporated. The brownish oil which remains behind crystallized upon triturating with diethyl ether/ligroin. After filtering off with suction and drying, there were obtained 18.6 g. (83% of theory) of lightly colored crystals; m.p. 118°-120° C.

18.5 g. of the 4-benzyloxy-6-hydroxymethylindole thus obtained were hydrogenated in 200 ml. methanol, with the addition of 3.0 g. of a palladium-charcoal catalyst (10:90), at atmospheric pressure and ambient temperature. After 2 hours, no starting material can be detected in a thin layer chromatogram. The catalyst was filtered off with suction and the filtrate was evaporated in a vacuum. The solid residue was intensively triturated with diethyl ether and filtered off with suction. There was obtained 10.0 g. (84% of theory 4-hydroxy-6-hydroxymethyl-indole; m.p. 168° - 169° C.

3.3 g. of the 4-hydroxy-6-hydroxymethyl-indole thus prepared were dissolved in 30 ml. epichlorohydrin. To this solution were added dropwise, while stirring at ambient temperature, over the course of 1 hour, 20 ml. 2N sodium methylate solution. After about 5 hours, the starting material had reacted. The solution was evaporated in a vacuum and the residue was mixed with water, as well as with a mixture of diethyl ether and ethyl acetate. The organic phase was shaken out several times with water, subsequently dried, treated with active charcoal and evaporated. The crude 4-(2,3-epoxypropoxy)-6-hydroxymethyl-indole thus obtained (about 5 g. of a brownish oil) contains, as by-product, some 4-(2-hydroxy-3-chloropropoxy)-6-hydroxymethyl-indole but was further used without further purification.

EXAMPLE 16

Preparation of 4-(2-hydroxy-3-isopropylaminopropoxy)-6-hydroxymethyl-indole

In the same manner as described in Example 15, from 5.1 g. 4-(2,3-epoxypropoxy)-6-hydroxymethyl-indole and 25 ml. isopropylamine, there were obtained 3.3 g. (41% of theory) 4-(2-hydroxy-3-isopropylamino-propoxy)-6-hydroxymethyl-indole in the form of its benzoate; m.p. 171° - 172° C.

EXAMPLE 17

Preparation of 4-(2-hydroxy-3-tert.-butylaminopropoxy)-6-methyl-indole 2.3 g. (4-(2,3-epoxypropoxy)-6-methyl-indole were dissolved in 25 ml. tert.-butylamine. The reaction mixture was left to stand for 3 days at ambient temperature and subsequently evaporated in a vacuum. The residue was subjected to an acidic separation in the manner described in Example 15. The residue (2.2 g.) thereby obtained was dissolved in a little ethyl acetate. Upon adding 1.0 g. benzoic acid, a crystalline precipitate gradually separates out. After filtering off with suction and drying, there was obtained 1.5 g. (33% of theory) 4-(2-hydroxy-3-tert.-butylaminopropoxy)-6-methyl-indole in the form of its benzoate; m.p. 198° - 200° C.

The 4-(2,3-epoxypropoxy)-6-methyl-indole used as starting material was obtained in the following manner:

A solution of 10.6 g. 4-benzyloxy-6-hydroxymethyl-indole (cf. the preparation of the starting material in Example 15) in 50 ml. pyridine was carefully mixed with 50 ml. acetic anhydride. The reaction mixture was left to stand overnight at ambient temperature and subsequently evaporated in a vacuum at 40° C. The residue was taken up in diethyl ether. The ethereal phase was successively washed with water, 1N sulfuric acid and again with water. The dried solution was treated with active charcoal and evaporated. There was obtained 9.9 g. (about 80% of theory) 4-benzyloxy-6-acetoxymethyl-indole which, as crude product, was further worked up; m.p. 98° - 100° C.

9.8 g. of the 4-benzyloxy-6-acetoxymethyl-indole thus obtained were hydrogenated in 200 ml. methanol with the addition of 2 g. of a palladium-charcoal catalyst (10:90). After about 3 hours, no more starting material was present. The catalyst was filtered off with suction and the filtrate was evaporated in a vacuum. The 4-hydroxy-6-methyl-indole obtained in almost 100% yield as a pale yellowish oil was, without purification, further reacted.

6.4 g. of crude 4-hydroxy-6-methyl-indole were reacted and further worked up with epichlorohydrin in the manner described in Example 15. The mixture of 4-(2,3-epoxypropoxy)-6-methyl-indole and 4-(2-hydroxy-3-chloropropoxy)-6-methyl-indole thereby obtained was chromatographed on a column of silica gel (elution with methylene chloride/methanol 99:1 - 95:5). In this way, there were obtained 2.8 g. (41.5% of theory, referred to the 4-benzyloxy-6-acetoxymethyl-indole) of chromatographically pure 4-(2,3-epoxy-propoxy)-6-methyl indole as an almost colorless oil.

EXAMPLE 18

Preparation of 4-(2-hydroxy-3-isopropylaminopropoxy)-6-methyl-indole

According to the process described in Example 17, from 4.0 g. 4-(2,3-epoxypropoxy)-6-methyl-indole and 25 ml. isopropylamine, there were obtained 3.0 g. (41% of theory) 4-(2-hydroxy-3-isopropylaminopropoxy)-6-methyl-indole in the form of its benzoate; m.p. 182° - 184° C.

EXAMPLE 19

Preparation of 4-[2-hydroxy-3-(1-methylthio-2-methylisopropylamino)-propoxy]-6-methyl-indole A mixture of 2.8 g. 4-(2,3-epoxypropoxy)-6-methyl-indole and 3.0 ml. 2,2-dimethyl-aziridine was left to stand for 2 days at ambient temperature. Excess 2,2-dimethyl-aziridine was removed in a vacuum. The residue was dissolved in a little isopropanol and subsequently mixed with 50 ml. of a solution of methyl mercaptan, saturated at 0° C., in isopropanol. After 2 days, the reaction mixture was evaporated in a vacuum. The residue was dissolved in 35 ml. ethyl acetate. After the addition of a solution of 1.7 g. benzoic acid in 10 ml. diethyl ether, a precipitate separates out. There were obtained 3.0 g. (50% of theory) 4-[2-hydroxy-3-(1-methylthio-2-methylisopropylamino)-propoxy]-6-methyl-indole in the form of its benzoate; m.p. 174° - 175° C.

EXAMPLE 20

Preparation of 4-(2-hydroxy-3-tert.-butylaminopropoxy)-6-pivaloyloxymethyl-indole 12.7 g. 4-(2,3-epoxypropoxy)-6-pivaloyloxymethyl-indole were kept for 2 days at ambient temperature in 50 ml. tert.-butylamine. Excess tert.-butylamine was then distilled off in a vacuum. The residue was dissolved in 1N acetic acid and the solution was extracted with diethyl ether. The aqueous phase was rendered alkaline with a dilute aqueous solution of potassium carbonate and shaken out with a mixture of diethyl ether/ethyl acetate. The organic phase was dried, treated with active charcoal and evaporated. The residue was dissolved in 50 ml. ethyl acetate and the solution mixed with 2.6 g. benzoic acid, dissolved in 30 ml. diethyl ether. The precipitate which was obtained was filtered off with suction and recrystallized from a 1:1 mixture of methanol and ethanol. There were obtained 5.3 g. (35% of theory) 4-(2-hydroxy-3-tert.-butylaminopropoxy)-6-pivaloyloxymethyl-indole in the form of its benzoate; m.p. 194° - 195° C.

The 4-(2,3-epoxypropoxy)-6-pivaloyloxymethyl-indole used as starting material was prepared as follows:

8.7 g. 4-(2,3-epoxypropoxy)-6-hydroxymethyl-indole (cf. the preparation of the starting material in Example 15) were dissolved in 50 ml. anhydrous pyridine. To this solution were added dropwise, while stirring and cooling to 5° - 10° C., 5 ml. pivalic acid chloride, 1.5 - 2 hours after the ending of the addition, the reaction mixture was poured into ice water. The aqueous phase was extracted 3 or 4 times with diethyl ether. The ethereal extract was successively washed with 1N sulfuric acid, a saturated aqueous solution of sodium bicarbonate and water, then dried, treated with active charcoal and fullers' earth and subsequently evaporated. The crude (4-(2,3-epoxypropoxy)-6-pivaloyloxymethyl-indole thus obtained (12.5 g.; about 100% of theory) was further reacted without further purification.

The following tests were carried out to determine the cardiac β-receptor blocking activity of certain test compounds by determining the inhibition of the heart beat frequency increase induced by intravenous administration of isoprenalin.

The test compounds representative of the invention were the following:

| | |
|---|---|
| Compound I: | 4-[2-Hydroxy-3-(1-methylmercapto-2-methyl-isopropylamino)propoxy]-indole |
| Compound II: | 4-(2-Hydroxy-3-tert.-butylamino-propoxy)-2-pivaloyloxymethyl-indole |
| Compound III: | 4-(2-Hydroxy-3-isopropylamino-propoxy)-2-pivaloyloxymethyl-indole |
| Compound IV: | 4-(2-Hydroxy-3-tert.-butylamino-propoxy)-6-hydroxymethyl-indole |
| Compound V: | 4-(2-Hydroxy-3-tert.-butylamino-propoxy)-6-methyl-indole |
| Compound VI: | 4-(2-Hydroxy-3-isopropylamino-propoxy)-6-methyl-indole |
| As comparison compounds there was included: | |
| Compound A: | 1-Isopropylamino-3-(1-naphthoxy)-2-propanol (Propranolol) |

These compounds were tested in the following manner:

The β-receptor blocking activity of the test compounds was tested on wake rabbits weighing between 2 to 3.5 kg and kept in wooden cages. EKG-electrodes were inserted into the hind quarters of the rabbits s.c. (II. lead) and the heart frequency was measured using an integrator (15 seconds) as a digital value. The test compounds were then infused through a small tube to the ear vein of the rabbits over a period of 15 minutes. 30 Minutes after the infusion isoprenalin (3,4-dihydroxy-α-[(isopropylamino)-methyl]-benzylalcohol) was injected intravenously at 1 μg/kg.

The results are set forth in terms of inhibition of isoprenalin tachycardia, and are set forth in the table below:

TABLE

| Test Substance | Blocking of Isoprenalin Tachycardia in Wake Rabbits: Dosage mg/kg i.v. | Heartbeat Frequency $\bar{x} \pm s_{\bar{x}}$ | ~$DE_{250^*}$ mg/kg i.v. |
|---|---|---|---|
| Control | without Isoprenaline | 205 ± 9 | — |
| Control | with Isoprenalin | 338 ± 10 | — |
| Compound A (Propranolol) | 0.01 | 342 ± 5 | 0.400 |
| | 0.1 | 309 ± 9 | |
| | 0.25 | 259 ± 7 | |
| | 0.5 | 248 ± 6 | |
| | 1.0 | 210 ± 8 | |
| | 4.0 | 191 ± 6 | |
| Compound I (Example 1) | 0.05 | 332 ± 6 | — |
| | 0.01 | 264 ± 6 | 0.140 |
| | 0.2 | 236 ± 10 | — |
| | 0.5 | 203 ± 9 | — |
| Compound II (Example 12) | 0.01 | 275 ± 3 | — |
| | 0.05 | 228 ± 10 | 0.020 |
| | 0.1 | 223 ± 8 | — |
| | 1.0 | 196 ± 11 | — |
| Compound III (Example 13) | 0.01 | 305 ± 14 | — |
| | 0.025 | 275 ± 6 | — |
| | 0.05 | 247 ± 10 | 0.090 |
| | 0.1 | 248 ± 7 | — |
| | 0.5 | 217 ± 7 | — |
| | 1.0 | 205 ± 5 | — |
| Compound IV (Example 15) | 0.05 | 268 ± 13 | — |
| | 0.1 | 283 ± 8 | 0.300 |
| | 0.5 | 238 ± 7 | — |
| | 1.0 | 222 ± 19 | — |
| Compound V (Example 17) | 0.01 | 278 ± 6 | — |
| | 0.02 | 239 ± 7 | — |
| | 0.05 | 217 ± 10 | 0.016 |
| | 1.0 | 206 ± 11 | — |
| | 5.0 | 247 ± 26 | — |
| Compound VI (Example 18) | 0.005 | 332 ± 6 | — |
| | 0.025 | 281 ± 12 | — |
| | 0.05 | 249 ± 5 | — |
| | 0.1 | 264 ± 9 | 0.090 |
| | 0.25 | 229 ± 7 | — |
| | 0.5 | 208 ± 9 | — |
| | 1.0 | 216 ± 8 | |

*Interpolated dosage which limits the frequency increase to 250 beats/min.

The above data show dosage that the inventive compounds are already effective at a dosage much smaller than those required of the comparison substances.

The compounds according to the present invention are thus unexpectedly superior in effectiveness to known compounds and thus present a valuable contribution to the art.

The dosage of the novel compounds of the present invention depend on the age, wieght, and condition of the patient being treated. Generally speaking, for adultoral administration, the preferred unit dosage of active compound with suitable pharmaceutical diluent or libricant is 1 mg. - 40 mg. four times a day. In general the oral dosage is 20 - 40 mg., whereas the intravenous dosage is generally 1 - 5 mg., four times a day.

For preparing therapeutic compositions such as tablets and other compressed formulations, the compounds can include any compatible and edible tableting material used in pharmaceutical practice as for example, corn starch, lactose, stearic acid, magnesium stearate, talc, methyl cellulose and the like.

Similarly the compounds of the present invention can be mixed with suitable adjuvants for the preparation of resorbable hard gelatin or soft capsules utilizing conventional pharmaceutical practices.

Further, the compounds can be employed in the form of their solutions or suspensions suitable for parenteral administrations.

It will be appreciated that the instant specification and examples are set forth by way of illustration and not limitation, and that various modifications and changes may be made without departing from the spirit and scope of the present invention.

What is claimed is:

1. Aminopropanol compound of the formula (I)

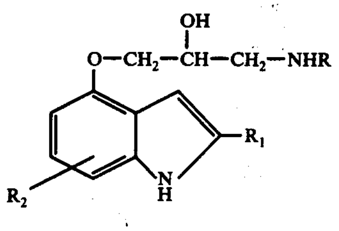

wherein

R is lower alkyl or cycloalkyl $R_1$ is hydrogen or lower alkyl, hydroxyalkyl, alkoxyalkyl, and $R_2$ is in the 6- position and is selected from lower alkyl, hydroxyalkyl, and alkoxyalkyl and the pharmacologically acceptable salts thereof.

2. Aminopropanol compound as claimed in claim 1 wherein R is alkyl of up to 6 carbon atoms.

3. Aminopropanol compound as claimed in claim 1 wherein R is cycloalkyl of from 3 to 6 ring carbon atoms.

4. Aminopropanol compound as claimed in claim 1 wherein $R_1$ is hydrogen.

5. Aminopropanol compound as claimed in claim 1 wherein $R_1$ is alkyl of up to 6 carbon atoms.

6. Aminopropanol compound as claimed in claim 1 wherein $R_1$ is hydroxyalkyl of up to 6 carbon atoms.

7. Aminopropanol compound as claimed in claim 1 wherein $R_1$ is alkoxyalkyl of up to 6 carbon atoms in each alkyl moiety.

8. Aminopropanol compound as claimed in claim 1 wherein $R_2$ is alkyl of up to 6 carbon atoms.

9. Aminopropanol compound as claimed in claim 1 wherein $R_2$ is hydroxyalkyl of up to 6 carbon atoms.

10. Aminopropanol compound as claimed in claim 1 wherein $R_2$ is alkoxyalkyl of up to 6 carbon atoms in each alkyl moiety.

11. Aminopropanol compound as claimed in claim 1 designated 4-(2-hydroxy-3-tert.-butylamino-propoxy)-6-hydroxymethyl-indole.

12. Aminopropanol compound as claimed in claim 1 designated 4-(2-hydroxy-3-tert.-butylamino-propoxy)-6-methyl-indole 13. Aminopropanol compound as claimed in claim 1 designated 4-(2-hydroxy-3-isopropylamino-propoxy)-6-methyl-indole.

14. Therapeutic composition for the treatment or prophylaxis of cardiac and circulatory diseases which composition comprises a pharmaceutically acceptable carrier and in amounts effective for treatment or prophylaxis of cardiac or circulatory diseases an aminopropanol compound as claimed in claim 1.

15. Method of combatting or preventing cardiac and circulatory infirmities which method comprises administering to a mammal in amounts effective for treatment or prophylaxis of cardiac or circulatory diseases an aminopropanol compound of the formula (I)

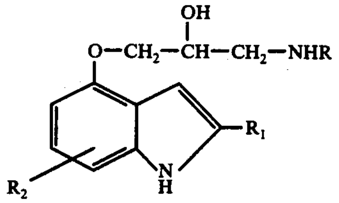

wherein

R is lower alkyl or cycloalkyl $R_1$ is hydrogen or lower alkyl, hydroxyalkyl, alkoxyalkyl, and $R_2$ is in the 6- position and is selected from lower alkyl, hydroxyalkyl, and alkoxyalkyl and the pharmacologically acceptable salts thereof.

16. Method as claimed in claim 15 wherein said compound is selected from 4-(2-hydroxy-3-tert.-butylamino-propoxy)-6-hydroxymethyl-indole, 4-(2-hydroxy-3-tert.-butylamino-propoxy)-6-methyl-indole, and 4-(2-hydroxy-3-isopropylamino-propoxy)-6-methyl-indole.

17. Method as claimed in claim 15 wherein said compound is applied at a dosage of 1 to 40 mg up to four times a day.

18. Method as claimed in claim 15 wherein said compound is applied orally in dosages of 20 to 40 mg.

19. Method as claimed in claim 15 wherein said compound is applied intravenously at a dosage of from 1 to 5 mg per dosage.

* * * * *